US012741160B2

(12) United States Patent
Fan et al.

(10) Patent No.: US 12,741,160 B2
(45) Date of Patent: Sep. 22, 2026

(54) LOCAL NEURAL NETWORK FOR THREE-DIMENSIONAL DOSE CALCULATIONS

(71) Applicant: Siemens Healthineers International AG, Steinhausen (CH)

(72) Inventors: Zheyong Fan, Espoo (FI); Petri Hiltunen, Espoo (FI); Ari Harju, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 996 days.

(21) Appl. No.: 17/978,698

(22) Filed: Nov. 1, 2022

(65) Prior Publication Data

US 2024/0139547 A1 May 2, 2024

(51) Int. Cl.
*A61N 5/10* (2006.01)
*G06N 3/08* (2023.01)

(52) U.S. Cl.
CPC ............. *A61N 5/1071* (2013.01); *G06N 3/08* (2013.01); *A61N 2005/1076* (2013.01)

(58) Field of Classification Search
CPC .......... A61N 5/1071; A61N 2005/1076; A61N 5/1031; G06N 3/08; G06N 3/088; G06N 3/0895; G06N 3/09; G06N 3/092; G06N 3/045; G06N 3/098; G16H 30/40; G16H 50/20; G16H 50/70; G16H 20/40
See application file for complete search history.

(56) References Cited

U.S. PATENT DOCUMENTS 8,065,244 B2 11/2011 Chen et al.
10,500,417 B2 12/2019 Kuusela et al.
10,850,121 B2 * 12/2020 Moore ................ A61N 5/1031
10,940,330 B2 3/2021 Ikonen et al.
11,020,615 B2 * 6/2021 Eriksson ................. G06N 7/01
11,282,192 B2 3/2022 Laaksonen et al.
11,358,003 B2 * 6/2022 Sjölund ................. A61N 5/103
(Continued)

OTHER PUBLICATIONS

Jianhui Ma et al., "Individualized 3D Dose Distribution Prediction Using Deep Learning" (Springer, Lecture Notes in Computer Science (LNCS) series 11850, pp. 110-118 (Year: 2019).*
(Continued)

*Primary Examiner* — Courtney D Thomas
(74) *Attorney, Agent, or Firm* — Foley & Lardner LLP

(57) ABSTRACT

Embodiments described herein provide for training a local neural network model that receives a first data set corresponding to parameters of a radiation therapy delivery system for delivering a radiation field to a phantom. The neural network model has been trained to determine the quantity of radiation delivered to a plurality of volume elements of the phantom based on the parameters of the first data set. The local neural network model receives local dose calculation parameters, such as total energy released per mass (TERMA) values and density values, for each voxel grid element of a high resolution voxel grid of the phantom. In an embodiment, each voxel grid element includes a central voxel and a plurality of neighboring voxels. The processor applies the neural network model to the TERMA values and the density values of the neighboring voxels to determine the quantity of radiation delivered to the central voxel.

20 Claims, 4 Drawing Sheets

(56) References Cited

U.S. PATENT DOCUMENTS

| | | | |
|---|---|---|---|
| 2013/0158879 | A1 | 6/2013 | Hu et al. |
| 2019/0192880 | A1 | 6/2019 | Hibbard |
| 2020/0075148 | A1 | 3/2020 | Nguyen et al. |
| 2021/0265071 | A1 | 8/2021 | Rochford et al. |
| 2022/0088410 | A1 | 3/2022 | Hibbard |
| 2022/0193448 | A1 | 6/2022 | Weese et al. |

OTHER PUBLICATIONS

International Search Report and Written Opinion on PCT App. PCT/EP2023/080261 dated Feb. 2, 2024 (13 pages).

Liu Zhiqiang et al: "A deep learning method for prediction of three-dimensional dose distribution of helical tomotherapy", Medical Physics, vol. 46, No. 5; Mar. 30, 2019 (Mar. 30, 2019), pp. 1972-1983, XP093122384, US ISSN: 0094-2405, DOI: 10.1002/mp.13490 Retrieved from the Internet: https://onlinelibrary.wiley.com/doi/full-xml/10.1002/mp.13490> abstract; figure 1chapter 2.B.

* cited by examiner

LOCAL NEURAL NETWORK FOR THREE-DIMENSIONAL DOSE CALCULATIONS

TECHNICAL FIELD

This application relates generally to modeling dose deposition for radiotherapy treatment.

BACKGROUND

Radiation therapy is a treatment using ionizing radiation for a specific tissue, such as a cancerous tumor. In planning treatment, a prescribing physician may identify a treatment location (e.g., patient's organ to be treated or tumor to be eradicated) and a corresponding dosage. Treatment planning may institute quality assurance and verification protocols using phantoms. Generally, determining how the dosage is delivered to the patient's tissue can be sub-divided into at least two tasks: modeling the radiation produced by a linear accelerator providing the radiation therapy (e.g., source modeling), and calculating/modeling the dosage received by a patient tissue or other material of interest (sometimes called dose calculation, also referred to as dosimetry).

In modeling dosimetry, artificial intelligence methods may be applied to simulate spatial and temporal patterns of energy deposition in a material of interest, e.g., patient tissue or phantom. Typically, existing artificial intelligence methods converge to a dose calculation solution by simulating entire patterns of energy deposition in the material of interest. Such methods are referred to herein as a global approach to dose calculation.

Existing artificial intelligence methods for dose calculation generally trade speed and accuracy. Certain existing artificial intelligence methods for dose calculation are more accurate, but may consume relatively high computational power and have long runtime. Other existing artificial intelligence methods consume less computational power and have reduced run-time, but generally are less accurate and require more memory.

SUMMARY

Disclosed systems and methods attempt to improve the accuracy and generalizability of artificial intelligence dosimetry models while maintaining high speed operation. Disclosed embodiments seek to improve dose distribution prediction of treatment volumes such as patient volumes and phantoms. In disclosed embodiments, neural network dosimetry models execute local three-dimensional dose calculations. Improved dose distribution models may be applied to various radiation therapy protocols such as dose calculation during inverse plan optimization, quality assurance (QA), and verification protocols. As treatment volume is used in the present application, the treatment volume may be a patient volume (e.g., patient tissue) or a phantom.

Embodiments described herein can speed up local calculations of energy deposition within a treatment volume and can reduce memory requirements for the local calculations. These embodiments address a limitation of existing dose calculation methods using a global approach. If there are too many voxels in such methods the dose calculation may run out of memory.

Embodiments described herein execute independent dose calculations in a local neural network model that can take into account heterogeneity of a treatment volume naturally without requiring restricting physical approximations. These embodiments address a limitation of existing dose calculation methods using pre-calculated dose-spreading kernel only for water, that such methods can give rise to large errors in calculated dose in a heterogeneous phantom or patient volume.

The system executes a neural network model to generate a three-dimensional radiation dose matrix, the three-dimensional radiation dose matrix indicating a quantity of radiation delivered to a plurality of volume elements of a treatment volume. The neural network model has been trained during a model training phase to determine the quantity of radiation delivered to the plurality of volume elements of the treatment volume based on the parameters indicated by a reference data set. The system applies the neural network model to local dose calculation parameters for each voxel grid element of a high resolution voxel grid of the treatment volume. The application of the neural network model to the local dose calculation parameters is independent for each voxel grid element.

In disclosed embodiments, the local dose calculation parameters for each voxel grid element comprise energy released per unit mass values and density values. In an embodiment, the energy released per unit mass values for each voxel grid element comprise Total Energy Released per Mass (TERMA) values. In various embodiments, the density values may indicate electron density or mass density.

In various embodiments, each voxel grid element includes a central voxel and a plurality of neighboring voxels. The system applies the neural network model to the local dose calculation parameters to determine the quantity of radiation delivered to the central voxel. In an embodiment, the system applies the neural network model to energy released per unit mass values and density values of the neighboring voxels to determine the quantity of radiation delivered to the central voxel.

In an embodiment, the processor applies a multiple-resolution grid algorithm to the high resolution voxel grid of the treatment volume. The multiple-resolution grid algorithm may be configured to down-sample the application of the neural network model to the energy released per mass values and the density values of the voxel grid elements, apply the neural network model to the down-sampled grid to determine quantity of radiation delivered to a plurality of volume elements of the treatment volume, and up-sample the determined quantity of radiation values.

In disclosed embodiments, the local neural network model has been trained during a previous model training phase by receiving a training data set representative of reference three-dimensional dose calculations for a plurality of training samples. In training of the local neural network model, a system receives a training data set corresponding to parameters of a radiation therapy delivery system for delivering a radiation field to a treatment volume such as a patient tissue or a phantom. In an embodiment, a training data set was comprised of a reference data set for a plurality of treatment volumes including one or more parameters: TERMA, density, and treatment dose in each voxel of the treatment volume. In various embodiments, the treatment dose can be obtained by an accurate calculation method or by experimental measurements. The local neural network model has been trained to determine the quantity of radiation delivered to one or more volume elements.

In an embodiment, the model training phase trains a local neural network model included in one or more end-user devices. The end-user device, such as clinic computer or clinic server, is configured to execute the trained local neural network model to generate a three-dimensional radiation dose matrix, e.g., during radiotherapy treatment of a patient. A local neural network dose calculation algorithm resulting from this training can be used to predict the dose for any voxel within any new treatment volume that is not used in the training process. In some embodiments, the treatment volume may be a patient target volume in calculating or modeling dosage to be received by the target volume.

In some embodiments, in the model training phase of the local neural network model, a system receives a training data set representative of reference dose calculations for a plurality of training samples. In an illustrative embodiment, this training data set was comprised of a large set of reference data set generated by a Linear Boltzmann Transport Equation algorithm.

In an embodiment, a method comprises receiving, by a processor, a first data set corresponding to parameters of a radiation therapy delivery system for delivering a radiation field to a treatment volume, wherein the treatment volume is a patient target or a phantom; and executing, by the processor, a neural network model to generate a three-dimensional radiation dose matrix for the treatment volume, the three-dimensional radiation dose matrix indicating a quantity of radiation delivered to a plurality of volume elements of the treatment volume, wherein the neural network model has been trained to determine the quantity of radiation delivered to the plurality of volume elements of the treatment volume based on the parameters indicated by the first data set, wherein the neural network model receives local dose calculation parameters for each voxel grid element of a high resolution voxel grid of the treatment volume, and wherein application of the neural network model to the local dose calculation parameters is independent for each respective voxel grid element of the high resolution voxel grid.

In an embodiment, a system comprises a server comprising a processor and a non-transitory computer-readable medium containing instructions that when executed by the processor causes the processor to perform operations comprising: receive a first data set corresponding to parameters of a radiation therapy delivery system for delivering a radiation field to a treatment volume, wherein the treatment volume is a patient volume or a phantom; and execute a neural network model to generate a three-dimensional radiation dose matrix for the treatment volume, the three-dimensional radiation dose matrix indicating a quantity of radiation delivered to a plurality of volume elements of the treatment volume, wherein the neural network model has been trained to determine the quantity of radiation delivered to the plurality of volume elements of the treatment volume based on the parameters indicated by the first data set, wherein the neural network model receives local dose calculation parameters for each voxel grid element of a high resolution voxel grid of the treatment volume, and wherein application of the neural network model to the local dose calculation parameters is independent for each respective voxel grid element of the high resolution voxel grid.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1:
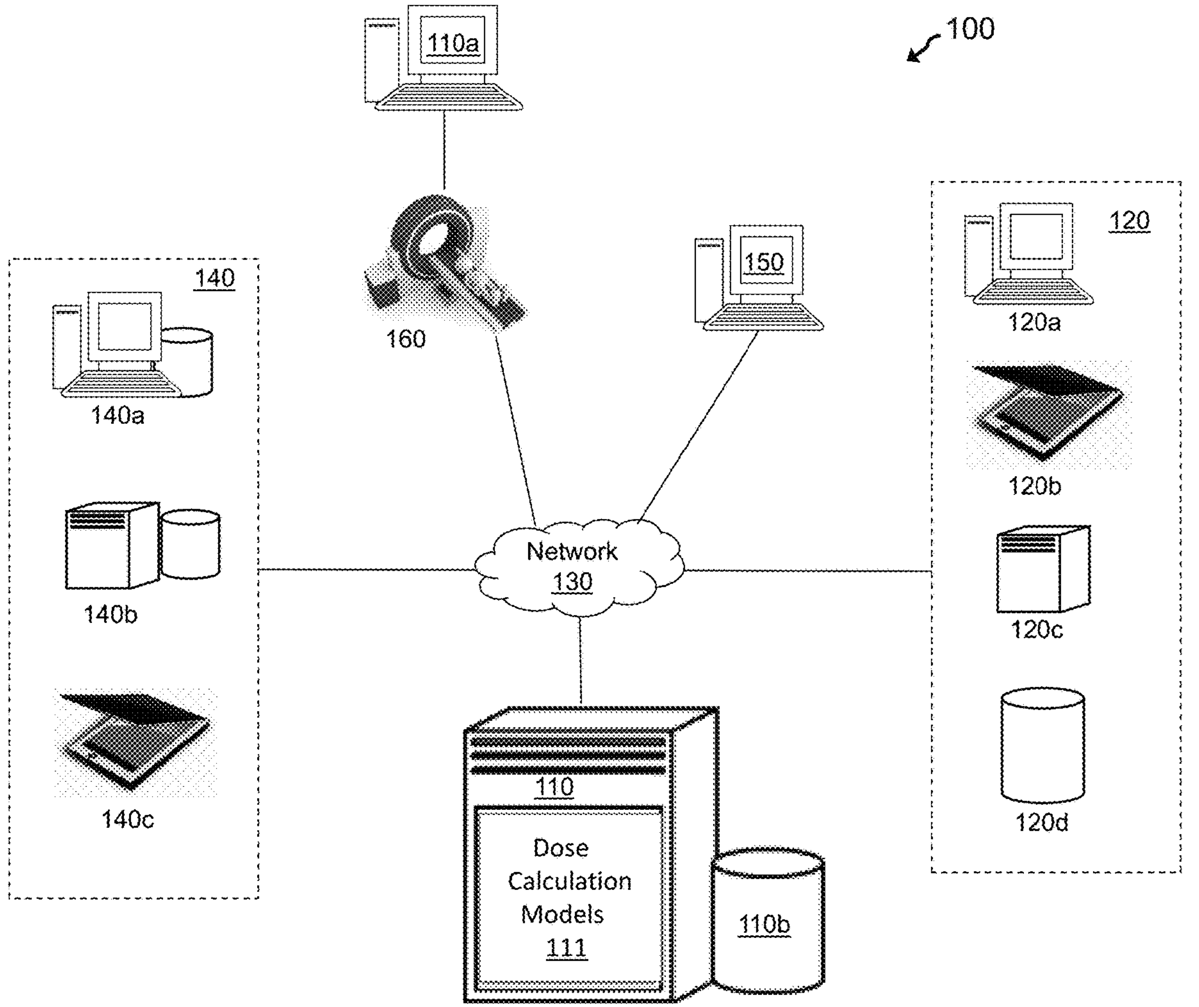
FIG. 1 illustrates components of a system for local neural network modeling of three-dimensional dose calculations, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Disclosed systems and methods for incorporate a local neural network for modeling of 3D dose calculations. The neural network model of the disclosure is sometimes referred to as local neural network model, sometimes abbreviated as "local NN model" or simply "local NN." For 3D dose calculation with external radiation beams, existing methods generally are either accurate but time consuming, or are faster but not very accurate. The local NN model of the disclosure attempts to improve the generalizability of the 3D dose calculation model compared to existing 3D dose calculation approaches.

For a successful outcome of patient radiation treatment it is imperative that the dose distribution is known precisely and accurately. Treatment planning (dosimetry) is responsible for preparing the treatment prescriptions for patients receiving radiation therapy by quantitatively analyzing the energy distribution from the ionizing radiation. Dose may be modeled via artificial intelligence ("AI") models executing three-dimensional ("3D") dose calculations. Dose or dose rate may be determined for a specific set of reference conditions, such as Depth in phantom Z, Field Size A, and Source-Surface Distance (SSD).

One existing method for modeling 3D dose calculations is Fourier Transform Dose Calculation. Fourier Transform Dose Calculation is sometimes abbreviated as "FTDC" in the present disclosure. To reduce burden on computational resources, a convolution operation in the spatial domain is implemented as a multiplication operation in the Fourier domain. The 3D dose is calculated as a convolution between the TERMA and a pre-calculated dose-spreading kernel. This kernel is only calculated for water and is used for general heterogeneous phantoms, which can give rise to large errors in the calculated dose. FTDC can have up to a few tens of percent error in low-density regions compared to measurements.

A further existing 3D dose calculation method is ACUROS® XB Advanced Dose Calculation Algorithm. This algorithm is sometimes abbreviated as AXB in the present disclosure. AXB solves and describes the macroscopic behavior of radiation particles numerically as they travel and interact with matter. The AXB algorithm belongs to the class of Linear Boltzmann Transport Equation (LBTE) solvers. The LBTE governs how particles stream through a medium, how particles scatter within the medium, and how particles are absorbed in the medium. Deterministic methods discretize the LBTE into a matrix and iteratively invert the matrix. The solution is a flux distribution (or fluence) that abstracts the particle reaction rate with the medium. AXB can achieve an accuracy of the order of 1-2% compared to measurements but can take one minute or more to calculate the 3D dose.

In performance comparisons of the local NN model of the disclosure to existing dose calculation methods, the speed of the local NN model has been close to that of FTDC. The accuracy of the local NN model has been generally higher than FTDC and in most cases very close to that of AXB.

The local NN model may be applied to various radiation therapy protocols such as dose calculation during inverse plan optimization, quality assurance (QA), and verification protocols, e.g., using phantom assemblies. Homogeneous and heterogeneous phantom materials can range from water to complex chemical mixtures that mimic the human body as it would interact with radiation. Water phantoms are a primary tool used for absolute dosimetry. Slab geometry phantoms are used for dosimetry and corrections for inhomogeneous geometries. Anthropomorphic phantoms are used for dosimetry measurements of typical or special treatment techniques.

Generally speaking, radiation dose calculation involves computing the amount of energy released via a radiation beam that is deposited within a region of interest within a patient. These areas of interest may be further broken down into small volume elements referred to as voxels. Dose calculations in phantoms also may be broken down into voxels. The size of these voxels changes depending on many different factors, including the calculation algorithm along with size and location of a target, e.g., tumor.

In conventional dose calculation techniques using a global approach, the amount of energy deposited in each voxel is accumulated within the region of interest and then the final dose may be calculated by dividing by average density of voxels in that region. In contrast to these conventional techniques, in the system and method of the disclosure the model receives local dose calculation parameters for each voxel grid element of a high resolution voxel grid of the treatment volume. In an embodiment, the model receives energy released per unit mass values and density values for each voxel grid element of a high resolution voxel grid of the treatment volume. The energy released per unit mass values and the density values is independent for each respective voxel grid element of the high resolution voxel grid. In various embodiments, the energy released per unit mass values for each voxel grid element comprise TERMA values. In various embodiments, the density values may indicate electron density or mass density.

Existing methods for 3D dose calculation using neural networks generally are based on a single large neural network. This single neural network takes the TERMA and density of the whole phantom as inputs and usually consists of a large number of hidden layers. In contrast, the local NN model of the disclosure takes TERMA and density using a high-resolution voxel grid of neural network elements. In an embodiment, these neural network elements are substantially identical. Each voxel grid element takes several TERMA and density values close to the calculation point as the inputs to the neural network and uses these to calculate the dose for a single voxel (central voxel). The independent dose calculation outputs the dose for the considered central voxel.

The local NN model can use memory more efficiently than the global approach in scaling from local calculations to dose calculations for a phantom because it performs the local calculations independently. In existing dose calculation methods using the global approach if the voxels are too numerous the dose calculation may run out of memory, e.g., in dose calculations for large patient volumes or large phantoms. In performance tests, when scaling up voxel count (number of voxels N) for various dose calculation methods, scaling of runtime was linear or even sublinear for the local NN model. Scaling of runtime was linear for a multiresolution pencil beam radiation dose calculation algorithm (herein referred to as "MRDC"). Scaling of runtime was superlinear [N*log(N)] for FTDC.

In disclosed embodiments, the local NN model has been trained using a training data set representative of reference 3D dose calculations for a plurality of training samples. The neural network model has been trained to determine the quantity of radiation delivered to one or more volume elements of the local NN model based on this training data set. In an illustrative embodiment, this training data set was comprised of a large set of reference data computed by AXB, including many phantoms and patient cases. Training the local NN model against the reference data computed by AXB determined the parameters in the local NN model. Updated local NN dose calculation algorithm resulting from this training can be used to predict the dose for any voxel within any new treatment volume that is not used in the training process. Training can be simplified because training is based on smaller neural network architectures (local voxel grid elements). The local NN model naturally takes into account heterogeneity of a treatment volume, and does not rely upon restricting physical approximations as in existing 3D dose calculation methods.

FIG. 1 illustrates components of an automated dose distribution analysis system 100. The system 100 may include an analytics server 110*a*, system database 110*b*, dose calculation models 111, electronic data sources 120*a-d* (collectively electronic data sources 120), end-user devices 140*a-e* (collectively end-user devices 140), and an administrator computing device 150. Various features depicted in FIG. 1 may perform dose distribution analysis on phantoms, such as dose calculation inside optimization. Various features depicted in FIG. 1 may belong to a radiotherapy clinic at which patients may receive radiotherapy treatment, in some cases via one or more radiotherapy machines located within the clinic (e.g., radiotherapy machine 140*d*).

The above-mentioned components may be connected to each other through a network 130. Examples of the network 130 may include, but are not limited to, private or public LAN, WLAN, MAN, WAN, and the Internet. The network 130 may include wired and/or wireless communications according to one or more standards and/or via one or more transport mediums. The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network.

The system 100 is not confined to the components described herein and may include additional or other components, not shown for brevity, which are to be considered within the scope of the embodiments described herein.

The analytics server 110*a* may generate and display an electronic platform configured to use local neural network models and other dose calculation models 111 (including AI models and/or machine-learning models) to identify and display dose distribution data. The electronic platform may include graphical user interfaces (GUIs) displayed on each electronic data source 120, the end-user devices 140, and/or the administrator computing device 150. An example of the electronic platform generated and hosted by the analytics server 110*a* may be a web-based application or a website configured to be displayed on different electronic devices, such as mobile devices, tablets, personal computer, and the like. The analytics server 110*a* may utilize the methods and systems described herein to optimize dosage distribution and display the results on the end-user devices or adjust the configuration of one of end-user devices 140 (e.g., the radiotherapy machine 140(1). The analytics server 110*a* may display the predicted dose distribution and/or radiation parameters on the clinic computer 120*a* or physician device 120*b*.

In a non-limiting example, a physician operating the physician device 120*b* may access the platform, input patient attributes or characteristics and other data, and further instruct the analytics server 110*a* to optimize the patient's treatment plan (e.g., dose distribution among the patient's organs). In another non-limiting example, a dosimetrist operating the clinic computer 120*a* may access the platform, input attributes for sample phantoms, and further instruct the analytics server 110*a* to output a dose distribution analysis e.g., for dose calculation inside optimization.

As described herein, radiation parameters may be or include any attributes related to using a radiotherapy machine, e.g., for treating patients at a radiotherapy clinic. Radiation parameters may include, but are not limited to, different treatment modalities, field geometry settings for external beam radiotherapy, side effect predictions, organ and/or tumor segmentation, machine therapy attributes, dosage administration attributes (e.g., dosage amount), treatment frequency, treatment timing, etc. The analytics server 110*a* may provide calibrated predictions for dose distribution for sample phantoms or for treating a patient.

The analytics server 110*a* may host a website accessible to users operating any of the electronic devices described herein (e.g., end users), where the content presented via the various webpages may be controlled based upon each particular user's role or viewing permissions. The analytics server 110*a* may be any computing device comprising a processor and non-transitory machine-readable storage capable of executing the various tasks and processes described herein. Non-limiting examples of such computing devices may include workstation computers, laptop computers, server computers, and the like. While the system 100 includes a single analytics server 110*a*, the analytics server 110*a* may include any number of computing devices operating in a distributed computing environment, such as a cloud environment.

The analytics server 110*a* may execute software applications configured to display the electronic platform (e.g., host a website), which may generate and serve various webpages to each electronic data source 120 and/or end-user devices 140. Different users may use the website to view and/or interact with the predicted results.

The analytics server 110*a* may be configured to require user authentication based upon a set of user authorization credentials (e.g., username, password, biometrics, cryptographic certificate, and the like). The analytics server 110*a* may access the system database 110*b* configured to store user credentials, which the analytics server 110*a* may be configured to reference in order to determine whether a set of entered credentials (purportedly authenticating the user) match an appropriate set of credentials that identify and authenticate the user.

The analytics server 110*a* also may store data associated with each user operating one or more electronic data sources 120 and/or end-user devices 140. The analytics server 110*a* may use the data to weigh interactions while training one or more dose calculation models 111. For instance, the analytics server 110*a* may indicate that a user is a medical professional whose inputs may be monitored and used to train the local NN model 111 described herein.

The analytics server 110*a* may generate a user interface (e.g., host or present a webpage) that presents information based upon a particular user's role within the system 100. In such implementations, the user's role may be defined by data fields and input fields in user records stored in the system database 110*b*. The analytics server 110*a* may authenticate the user and may identify the user's role by executing an access directory protocol (e.g. LDAP). The analytics server 110*a* may generate webpage content that is customized according to the user's role defined by the user record in the system database 110*b*.

The electronic data sources 120 may represent various electronic data sources that contain, retrieve, and/or input data associated with phantoms, and data associated with patients and their treatment (e.g., patient data, treatment plans, and radiation parameters). For instance, the analytics server 110*a* may use the clinic computer 120*a*, physician device 120*b*, server 120*c* (associated with a physician and/or clinic), and database 120*d* (associated with the physician and/or the clinic) to retrieve/receive data associated with a particular patient's treatment plan.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110*a*. Specifically, the end-user devices 140 may include clinic computer 140*a*, clinic database 140*b*, clinic server 140*c*, a medical device, such as a CT scan machine, radiotherapy machine (e.g., a linear accelerator, cobalt machine or the like) 140*d*, and a clinic device 140*e*.

The administrator computing device 150 may represent a computing device operated by a system administrator. The administrator computing device 150 may be configured to display data retrieved and/or radiation parameters generated by the analytics server 110*a* (e.g., various analytic metrics and/or field geometry) where the system administrator can monitor various models 111 utilized by the analytics server 110*a*, electronic data sources 120, and/or end-user devices 140; review feedback; and/or facilitate training or calibration of the neural networks that are maintained by the analytic server 110*a*.

The analytics server 110*a* may be in communication (real-time or near real-time) with the medical device 140*d*, such that a server/computer hosting the medical device 140*d* can adjust the medical device 140*d* based on the radiation parameters generated by the analytics server 110*a*. For instance, the radiotherapy machine may adjust the gantry and couch based on angles and other attributes/parameters determined by the analytics server 110*a*. The analytics server 110*a* may transmit instructions to the radiotherapy machines indicating any number or type of radiation parameters (e.g., field geometry settings) to facilitate such adjustments.

The analytics server 110*a* may store AI models 111 (e.g., the local NN model) that have been trained to predict 3D dose distribution of treatment volumes, e.g., patient treatment volumes or phantoms. During a model training phase the analytics server 110*a* may train the 3D dose distribution models 111 using treatment volume data previously calculated, and using patient data and treatment data associated with patients who were previously treated. The analytics server 110*a* may generate one or more sets of labeled (or sometimes unlabeled) training dataset indicating radiation parameters that were used to treat the patients (and whether they are acceptable or not). The analytics server 110*a* may input the set of labeled training dataset into the stored AI models 111 for training (e.g., supervised, unsupervised, and/or semi-supervised) to train the AI models 111 to predict dose distribution for future treatments. The analytics server 110*a* may continue to feed the training data into the AI models 111 until the AI models 111 are accurate to a desired threshold and store the AI models 111 in a database, such as the database 110*b*. In the illustration of FIG. 1, AI models 111 are shown as being executed by the analytics server 110*a*, but may be stored on analytics server 110*a* or system database 110*b*.

The 3D dose calculation models stored in the database 110*b* may correspond to individual radiotherapy clinics or otherwise different sets of radiotherapy machines (e.g., located at individual radiotherapy clinics, are located in different geographical regions, treat specific types of diseases (e.g., different type of cancers), treat specific genders, etc.). For example, each 3D dose calculation model 111 may be associated with an identifier indicating the radiotherapy clinic, set of radiotherapy machines, or a specific disease for which it is configured to predict dose distribution data.

An operator at a radiotherapy clinic may access an end-user device 140 located at the clinic or access an account associated with the clinic. The operator may provide an input at a user interface that causes the end-user device 140 to transmit a request to access a particular 3D dose calculation model 111 that is associated with the clinic and/or the radiotherapy machines located within the clinic. The request may include an identifier associated with the dose calculation model 111, the clinic, and/or the set of radiotherapy machines that the analytics server 110*a* may use as a key in a look-up table to identify the desired dose calculation model 111. The analytics server 110*a* may receive the request and, in some cases, after authenticating the user, identify the AI model 111 via the identifier. The analytics server 110*a* may transmit the identified dose calculation model 111 to the end-user device 140 or send an alert indicating the end-user device is authorized to access the identified dose calculation model 111. Upon receipt or access to the dose calculation model 111, the end-user device 140 may perform the systems and methods described herein to execute the AI model 111 to predict dose distribution data for a phantom or for a patient.

Figure 2:
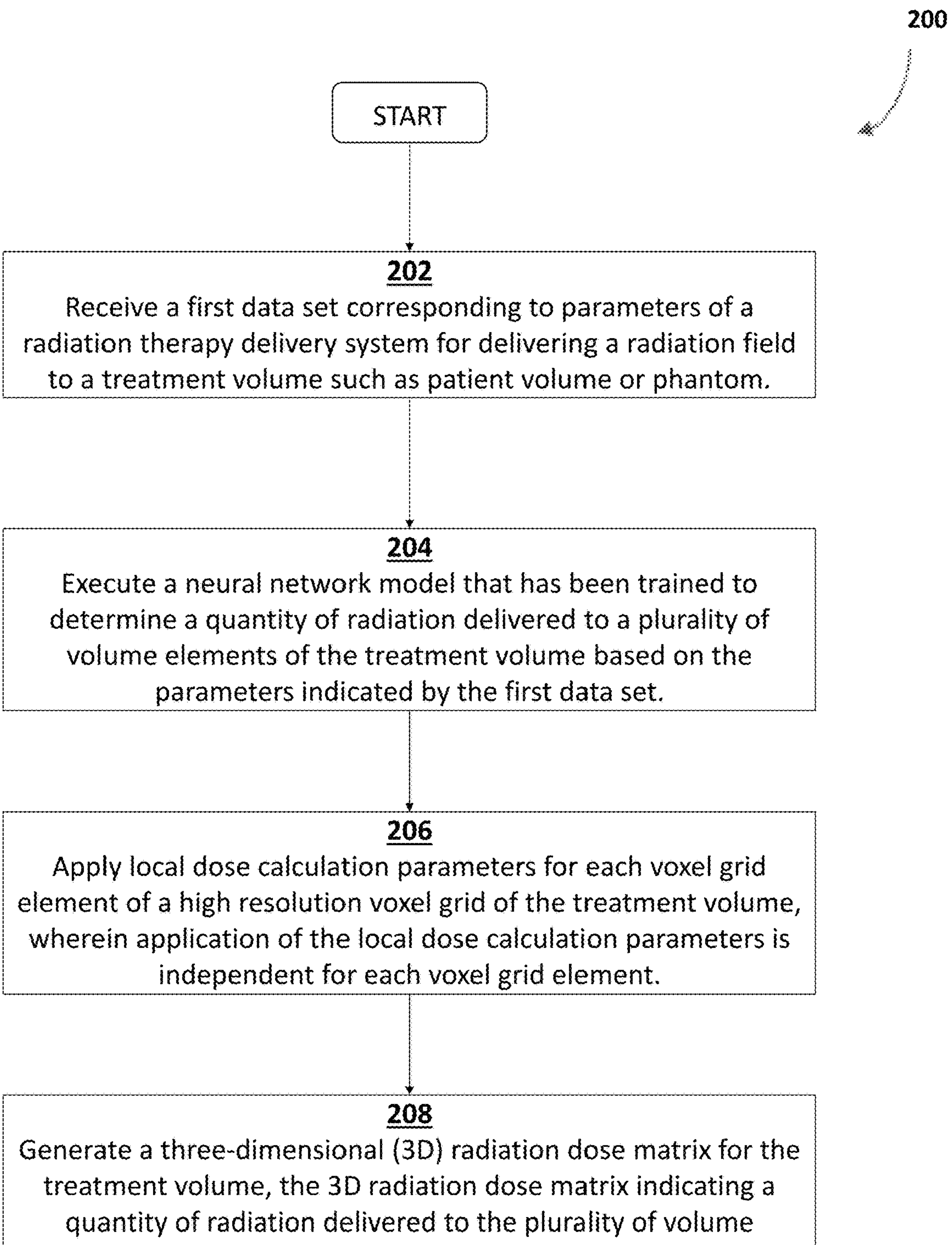
FIG. 2 illustrates a flow diagram of a process for local neural network modeling of three-dimensional dose calculations, according to an embodiment.

FIG. 2 illustrates a flow diagram of a process for local neural network modeling of 3D dose calculations. The method 200 may include steps 202-208. However, other embodiments may include additional or alternative steps, or may omit one or more steps altogether.

In an embodiment, the method 200 is executed by an analytics server, such as the analytics server described in FIG. 1. The analytics server may employ one or more processing units, including but not limited to CPUs, GPUs, or TPUs, to perform one or more steps of method 200. The CPUs, GPUs, and/or TPUs may be employed in part by the analytics server and in part by one or more other servers and/or computing devices. The servers and/or computing devices employing the processing units may be local, remote, or some combination. For example, one or more virtual machines in a cloud may employ one or more processing units, or a hybrid processing unit implementation, to perform one or more steps of method 200. However, one or more steps of method 200 may be executed by any number of computing devices or processors. For instance, one or more processors may locally perform part or all of the steps described in FIG. 2.

In step 202, the processor receives a first data set corresponding to parameters of a radiation therapy delivery system for delivering a radiation field to a treatment volume. In various embodiments, the treatment volume may be a patient volume or a phantom. In various embodiments, the first data set includes one or more of a field angle, a field strength, and a field aperture of the radiation field.

In step 204, the processor executes a neural network model that has previously been trained to determine the quantity of radiation delivered to a plurality of volume elements of the treatment volume based on the parameters indicated by the first data set.

In step 206, as a result of executing the neural network, the processor applies local dose calculation parameters for each voxel grid element of a high resolution voxel grid of the treatment volume. As depicted in step 206, the application of the local dose calculation parameters may be independent for each voxel grid element.

In an embodiment of step 206, the local dose calculation parameters may comprise energy released per unit mass values and density values for each voxel grid element of a high resolution voxel grid of the treatment volume. The application of the neural network model to the energy released per unit mass values and density values may be independent for each voxel grid element.

In an embodiment of step 206, the energy released per unit mass values for each voxel grid element comprise Total Energy Released per Mass (TERMA) values. In computing the TERMA at each local grid element, TERMA, $T_E(r')$ of a particular energy E at point r' may be defined as the fluence of energy E, $\Psi_E(r')$, weighted by the mass density relative to water, $\rho(r')$, and linear attenuation, $\mu_E(r')$. In other embodiments, the energy released per unit mass values can include a kinetic energy released per unit mass (KERMA) and/or scatter energy released per unit mass (SCERMA) calculation. In various embodiments, the density values may indicate electron density or mass density.

In step 208, the processor generates a 3D radiation dose matrix for the treatment volume. The 3D radiation dose matrix indicates a quantity of radiation delivered to the plurality of volume elements of the treatment volume.

In an embodiment, each voxel grid element comprises a central voxel and a plurality of neighboring voxels. The processor applies the neural network model to the local dose calculation parameters of the neighboring voxels to determine the quantity of radiation delivered to the central voxel.

In an embodiment, the processor applies a multiple-resolution grid algorithm to the high resolution voxel grid of the treatment volume. In this embodiment, the processor may apply a multiple-resolution grid algorithm to the high resolution voxel grid of the treatment volume. The multiple-resolution grid algorithm may be configured to down-sample the application of the neural network model to the energy released per mass values and the density values of the voxel grid elements, apply the neural network model to the down-sampled grid to determine quantity of radiation delivered to a plurality of volume elements of the treatment volume, and up-sample the determined quantity of radiation values. The multiple-resolution grid algorithm can speed up operation of the local NN model, similar to MRDC.

In an embodiment, the local NN model has been trained using a natural evolution algorithm. In contrast to training using conventional gradient descent based optimization algorithms, training using a natural evolution algorithm allows defining a complicated loss function that has no analytical properties as required by machine learning libraries. This can avoid initialization overhead and can achieve improved computational performance.

In an embodiment, the local NN model has been trained using training data set representative of reference 3D dose calculations for a plurality of training samples. The neural network model has been trained to determine the quantity of radiation delivered to one or more volume elements based on the training data set. The training samples may include patient tissue samples, e.g., with 3D dose calculations for previously treated patients. The training samples may include a plurality of radiation fluence distributions. The processor may apply information for the training samples (e.g., physical attributes of phantoms, or treatment attributes of patients and other data produced by a treating physician) to the trained AI model. As a result, the trained neural network model may predict new dose distribution values.

In an embodiment, the reference 3D dose calculations were generated by applying a Linear Boltzmann Transport Equation algorithm to the plurality of training samples. In an embodiment, the reference dose calculations applied an ACUROS® XB Advanced Dose Calculation Algorithm ("AXB") to the training samples.

A model training phase may train the local NN model using various machine-learning methodologies. The analytics server may train the local NN model using supervised, semi-supervised, and/or unsupervised training or using a reinforcement learning approach. For example, the local NN model may be trained to predict dosage distribution for a patient. To do so, characteristic values of individual patients within the training dataset may be ingested by the local NN model with labels indicating the correct predictions for the patients (e.g., examples of acceptable and unacceptable dosage distribution). The local NN model may output dose distribution values for individual phantoms or patients based on their respective characteristics, and the outputs can be compared against the labels. The analytics server may continue this training process until the local NN model is sufficiently trained (e.g., accurate above a predetermined threshold). The computer may store the AI model in memory, in some cases upon determining the local NN model has been sufficiently trained.

Figure 3:
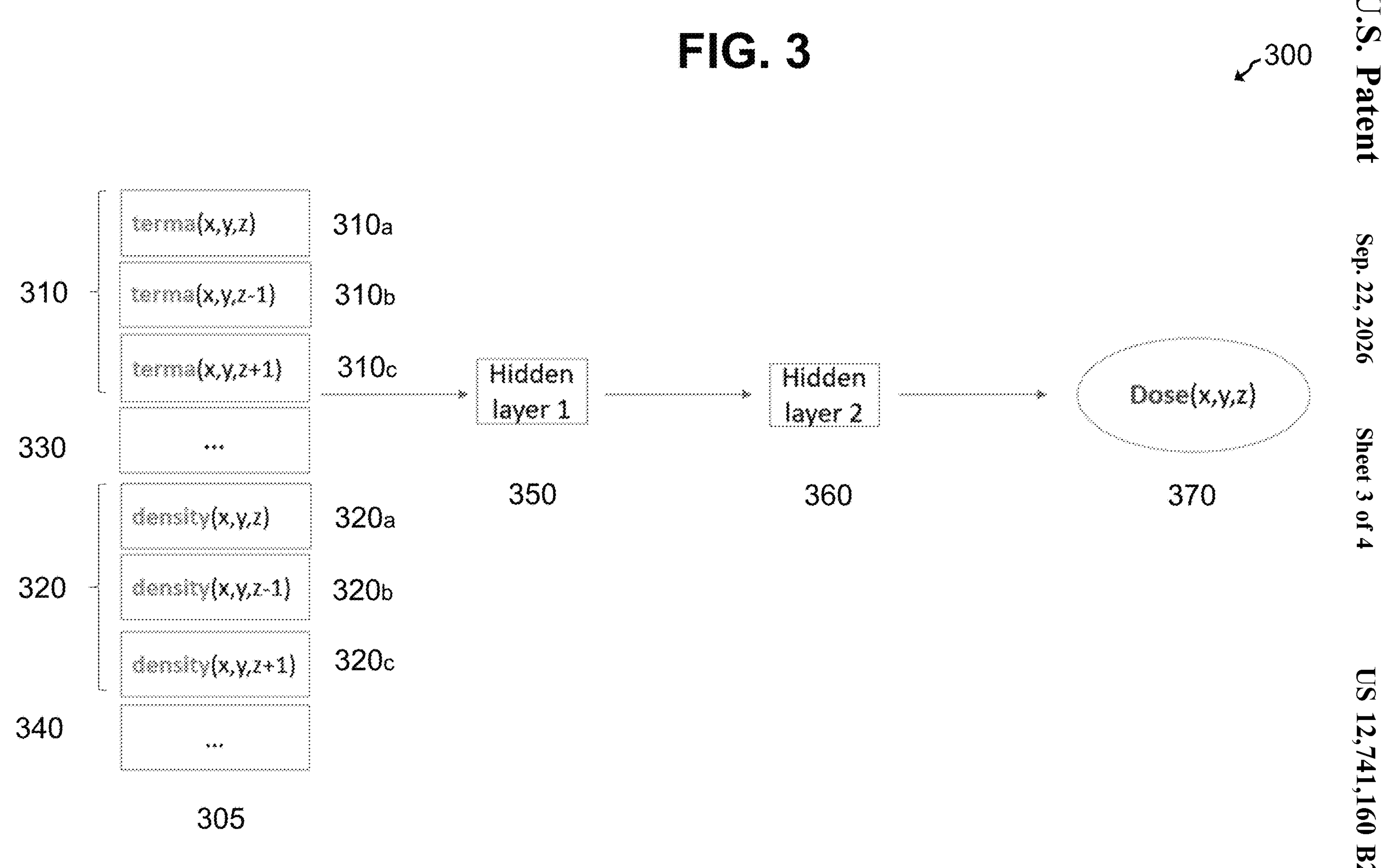
FIG. 3 illustrates an architecture of a local neural network model of three-dimensional dose calculations, according to an embodiment.

In an example local neural network architecture shown in FIG. 3, a given grid element for a local NN model is designed as 3D NN 300. 3D NN 300 includes an input layer 305 followed by two or more hidden layers (e.g., hidden layers 350 and 360) and output layer 370. Neurons in the layers of 3D NN 300 are arranged in three dimensions (width (x), height (y), and depth (z)). In an embodiment, the input layer 305 is a 3D grid of elements 310, 320, 330, 340 with dimensions Nx, Ny, Nz.

In an embodiment, the local NN model grid element includes a central voxel (x, y, z) and a plurality of neighboring voxels. The input layer 305 consists of neighboring voxels of the central voxel at output layer 370. The input layer 305 includes terma parameters 310 for neighboring voxels including terma(x, y, z) 310*a*, terma(x, y, z−1) 310*b*, and terma(x, y, z+1) 310*c*. The input layer 305 includes density parameters 320 for neighboring voxels including density(x, y, z) 320*a*, density(x, y, z−1) 320*b*, and density (x, y, z+1) 320*c*. FIG. 3 shows a limited set of neighboring voxels. Additional examples could include neighboring voxels on the width (x) axis such as terma(x−1, y, z) and terma(x+1, y, z). Additional examples could include a larger range of neighboring voxels such as terma(x, y, z+2) and terma(x+1, y, z−2). Additional examples could include combinations of variations of width (x), height (y), and depth (z).

The output layer 370 calculates dose for the central voxel (x, y, z) in an independent calculation based on the terma and density parameters for the local NN voxel grid element 300.

Figure 4:
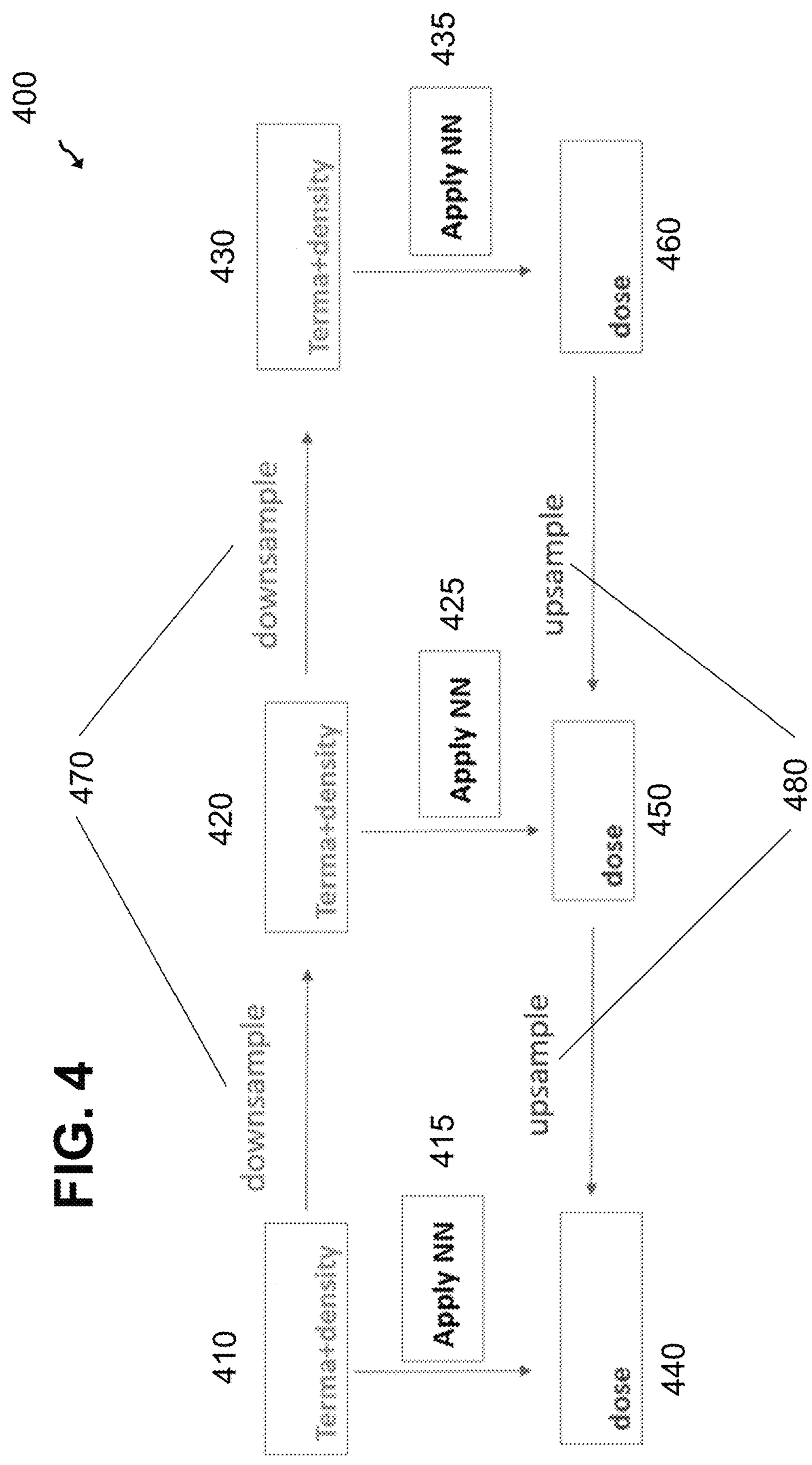
FIG. 4 illustrates a process for applying a multiple-resolution grid algorithm to a local neural network model of three-dimensional dose calculations, according to an embodiment.

FIG. 4 illustrates a process 400 for applying a multiple-resolution grid algorithm to the high resolution voxel grid of the treatment volume. The multiple-resolution grid algorithm 400 may include a number of downsample/upsample operations. Three downsample/upsample operations are shown in FIG. 4. The process may include a grid 410 for TERMA of any size (e.g., 2.5 mm)+density input parameters, grid 420 for TERMA of any size (e.g., 5 mm)+density input parameters, and grid 430 for TERMA of any size (e.g., 10 mm)+density input parameters. At 415, 425, 435 the local NN applies the input parameters to generate dose outputs. The multiple-resolution grid algorithm further includes a grid 440 of any size (e.g., 2.5 mm) for dose output, a grid 450 of any size (e.g., 5.0 mm) for dose output, and a grid 460 of any size (e.g., 10 mm) for dose output.

The multiple-resolution grid algorithm 400 may be configured to down-sample 470 the application of the neural network model to energy released per mass values and the density values of the voxel grid elements, and to apply the neural network model to the down-sampled grid to determine dose outputs of the voxel grid elements 440, 450, and 460. The local NN model may be configured to utilize down-sampling as many times as needed. For instance, even though the down-sampling 470 is shown as being performed two times (between the grids 410 and 420 and between grids 420 and 430), other embodiments may include fewer or more down-samplings.

The multiple-resolution grid algorithm may be configured to apply the neural network model to the down-sampled grid to determine dose outputs of the voxel grid elements 440, 450, and 460, and to up-sample 480 the determined dose outputs. The local NN model may be configured to utilize up-sampling as many times as needed. For instance, even though the up-sampling 480 is shown as being performed two times (between the grids 440 and 450 and between grids 450 and 460), other embodiments may include fewer or more up-samplings. The algorithm can speed up operation of the local NN model, similar to MRDC algorithm.

The systems and methods discussed herein may apply to any grid size. Therefore, the grid sizes discussed herein are non-limiting examples of sizes that could be used.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A method comprising:

receiving, by a processor, a first data set corresponding to parameters of a radiation therapy delivery system for delivering a radiation field to a treatment volume, wherein the treatment volume is a patient volume or a phantom; and executing, by the processor, a neural network model to generate a three-dimensional radiation dose matrix for the treatment volume, the three-dimensional radiation dose matrix indicating a quantity of radiation delivered to a plurality of volume elements of the treatment volume, wherein the neural network model has been trained to determine the quantity of radiation delivered to the plurality of volume elements of the treatment volume based on the parameters indicated by the first data set, wherein the neural network model receives local dose calculation parameters for each voxel grid element of a high resolution voxel grid of the treatment volume, and wherein application of the neural network model to the local dose calculation parameters is independent for each respective voxel grid element of the high resolution voxel grid.

2. The method of claim 1, wherein the local dose calculation parameters for each voxel grid element comprise total energy released per mass (TERMA) and density values.

3. The method of claim 2, wherein the density values indicate electron density or mass density.

4. The method of claim 1, wherein each voxel grid element comprises a central voxel and a plurality of neighboring voxels.

5. The method of claim 4, wherein the processor applies the neural network model to the local dose calculation parameters of the neighboring voxels to determine the quantity of radiation delivered to the central voxel.

6. The method of claim 1, wherein the processor applies a multiple-resolution grid algorithm to the high resolution voxel grid of the treatment volume.

7. The method of claim 6, wherein the neural network model is configured to down-sample the application of the neural network model to the energy released per mass values and the density values of the voxel grid elements, and is configured to up-sample the determined quantity of radiation delivered to the plurality of volume elements of the treatment volume.

8. The method of claim 1, wherein the local neural network model has been trained by receiving a training data set representative of reference three-dimensional dose calculations for a plurality of training samples, wherein the local neural network model has been trained to determine the quantity of radiation delivered to one or more volume elements.

9. The method of claim 8, wherein the plurality of training samples include patient tissue samples.

10. The method of claim 8, wherein the plurality of training samples include a plurality of photon fluence distributions.

11. The method of claim 8, wherein the reference three-dimensional dose calculations were generated by a Linear Boltzmann Transport Equation algorithm.

12. The method of claim 1, wherein the neural network model has been trained using a natural evolution algorithm.

13. The method of claim 1, wherein the first data set includes one or more of a field angle, a field strength, and a field aperture of the radiation field.

14. A system comprising:

a server comprising a processor and a non-transitory computer-readable medium containing instructions that when executed by the processor causes the processor to perform operations comprising:

receive a first data set corresponding to parameters of a radiation therapy delivery system for delivering a radiation field to a treatment volume, wherein the treatment volume is a patient volume or a phantom; and execute a neural network model to generate a three-dimensional radiation dose matrix for the treatment volume, the three-dimensional radiation dose matrix indicating a quantity of radiation delivered to a plurality of volume elements of the treatment volume, wherein the neural network model has been trained to determine the quantity of radiation delivered to the plurality of volume elements of the treatment volume based on the parameters indicated by the first data set, wherein the neural network model receives local dose calculation parameters for each voxel grid element of a high resolution voxel grid of the treatment volume, and wherein application of the neural network model to the local dose calculation parameters is independent for each respective voxel grid element of the high resolution voxel grid.

15. The system of claim 14, wherein the wherein the local dose calculation parameters for each voxel grid element comprise total energy released per mass (TERMA) and density values.

16. The system of claim 15, wherein the density values may indicate electron density or mass density.

17. The system of claim 14, wherein each voxel grid element comprises a central voxel and a plurality of neighboring voxels.

18. The system of claim 17, wherein the processor applies the neural network model to the local dose calculation parameters of the neighboring voxels and the density values of the neighboring voxels to determine the quantity of radiation delivered to the central voxel.

19. The system of claim 14, wherein the processor applies a multiple-resolution grid algorithm to the high resolution voxel grid of the treatment volume.

20. The system of claim 14, wherein the neural network has been trained using a training data set representative of reference three-dimensional dose calculations for a plurality of training samples, wherein the neural network model has been trained to determine the quantity of radiation delivered.

* * * * *